United States Patent
Dinh

(10) Patent No.: US 12,339,230 B2
(45) Date of Patent: Jun. 24, 2025

(54) PORTABLE MODULAR UNIT FOR INSPECTING IN A TIMEPIECE THE PRESENCE OF A LUBRICATING AGENT OR OF AN EPILAME

(71) Applicant: The Swatch Group Research and Development Ltd, Marin (CH)

(72) Inventor: Jean-Bosco Thanh Khai Dinh, Fribourg (CH)

(73) Assignee: The Swatch Group Research and Development Ltd, Marin (CH)

( * ) Notice: Subject to any disclaimer, the term of this patent is extended or adjusted under 35 U.S.C. 154(b) by 280 days.

(21) Appl. No.: 17/873,713

(22) Filed: Jul. 26, 2022

(65) Prior Publication Data

US 2023/0048871 A1    Feb. 16, 2023

(30) Foreign Application Priority Data

Aug. 13, 2021  (EP) .................................... 21191299

(51) Int. Cl.
*G01N 21/64*   (2006.01)
*G01N 33/30*   (2006.01)
(Continued)

(52) U.S. Cl.
CPC ......... *G01N 21/6447* (2013.01); *G01N 33/30* (2013.01); *G02B 25/007* (2013.01); *G02B 25/02* (2013.01); *G04D 7/004* (2013.01)

(58) Field of Classification Search
CPC ............. G01N 21/643; G01N 21/6447; G02B 25/007; G02B 25/02
See application file for complete search history.

(56) References Cited

U.S. PATENT DOCUMENTS

| | | | |
|---|---|---|---|
| 6,345,115 B1 * | 2/2002 | Ramm | G06T 7/73 |
| | | | 382/128 |
| 9,464,329 B2 * | 10/2016 | Cargill | G01N 21/643 |
| 2009/0127475 A1 * | 5/2009 | De Lamberterie | ......... |
| | | | G01N 21/6447 |
| | | | 250/484.4 |

FOREIGN PATENT DOCUMENTS

| | | | | |
|---|---|---|---|---|
| JP | WO2014013720 A1 * | 6/2016 | ............. | G02B 21/06 |
| WO | 2006/077304 A1 | 7/2006 | | |

(Continued)

OTHER PUBLICATIONS

Anonymous, "Amazon.com: Qooltek Bracket/Headband Magnifying Glass Jewelry Clock Repair Loupe", website, URL: https://www.amazon.com/Oooltek-Headban.d-Magnifying-Interchangeable-Upgraded/dp/B078JPRH2Y/ref=pd_dav0_1/138-1801601-1391437?pd_rd_w=DA4Ox&pf_rd_p=8ca997d7-lea0-4c8f-9el4-a6d756b83e30&pf_rd_r=QYXAGPXBYYXAZV8TPVYK&pd&rd_r=d432d58d-caf0-4b2f-ba63-8dl38f2f620b&pd_rd_wg=4hldj&pd_rd_i=B078JPRH27&th =1, retrieved on Aug. 9, 2021, 11 pages, XP055830882.

(Continued)

*Primary Examiner* — David P Porta
*Assistant Examiner* — Miya Downing
(74) *Attorney, Agent, or Firm* — Sughrue Mion, PLLC

(57) ABSTRACT

A portable modular unit for inspecting in a timepiece the presence of a lubricating agent, or of an epilame, having fluorescent markers, from an excitation luminous flux of white light. The modular unit includes an optical housing forming a first module, a portable white light source (200) emitting an excitation luminous flux forming a second module, and a portable magnifying device forming a third module. The optical housing includes a first mounting interface for removably mounting the portable white light source on the optical housing, the first mounting interface (Continued)

being configured so that the excitation luminous flux emitted by the portable white light source is directed in the direction of the excitation filter; and a second mounting interface for removably mounting the portable magnifying device on the optical housing, the second mounting interface being configured so that the magnifying device is opposite the inspection opening.

12 Claims, 3 Drawing Sheets

(51) Int. Cl.
  *G02B 25/00* (2006.01)
  *G02B 25/02* (2006.01)
  *G04D 7/00* (2006.01)

(56) References Cited

FOREIGN PATENT DOCUMENTS

| | | |
|---|---|---|
| WO | 2011/002209 A2 | 1/2011 |
| WO | 2011/002209 A3 | 1/2011 |
| WO | WO-2014013720 A1 * | 1/2014 ............. G02B 21/06 |

OTHER PUBLICATIONS

European Search Report of EP 21 19 1299.3 dated Jan. 20, 2022.

* cited by examiner

PORTABLE MODULAR UNIT FOR INSPECTING IN A TIMEPIECE THE PRESENCE OF A LUBRICATING AGENT OR OF AN EPILAME

CROSS REFERENCE TO RELATED APPLICATIONS

This application is claiming priority based on European Patent Application No. 21191299.3 filed on Aug. 13, 2021, the disclosure of which is incorporated herein in its entirely by reference.

TECHNICAL FIELD OF THE INVENTION

The field of the invention relates to the inspection, the revision and the maintenance of timepieces.

More particularly, the invention relates to a portable modular unit making it possible to combine and modulate various horological equipment commonly used for inspecting a timepiece, and more particularly for controlling the presence of a lubricating agent or of an epilame having fluorescent markers in a timepiece under excitation of a luminous flux of white light.

TECHNOLOGICAL BACKGROUND

Lubricating agents exist, such as oils, greases, or epilames integrating in their composition fluorescent markers facilitating their visibility when these lubricating agents or these epilames are subjected to a particular luminous excitation.

The use of these lubricating agents, or epilames, comprising such fluorescent markers, is particularly appreciated for the inspection and maintenance of a horological movement having a large number of parts and lubricating points.

These fluorescent markers emit a green light under the excitation of a luminous flux having a wavelength range between approximately 350 nm and 480 nm.

Thus, it is possible to excite these fluorescent markers by means of an ultraviolet (UV) radiation light source (wavelength less than 400 nm) that is notoriously harmful for eyes, or by means of a blue light source (wavelength in the order of 470 nm) by using a plurality of optical filters to obtain the wavelength, or the wavelength range, desired for the excitation of fluorescent markers.

However, none of these solutions is entirely satisfactory, because this requires either providing a particular visual protection, or providing a particular blue light source to excite the fluorescent markers.

Consequently, there is a need to facilitate the inspection in the timepieces of these lubricating agents or of these epilames having fluorescent markers.

SUMMARY OF THE INVENTION

In this context, the invention proposes a portable modular unit for inspecting in a timepiece the presence of a lubricating agent or of an epilame having fluorescent markers, of simple design, easy to implement and making it possible to simplify this inspection operation taking place during various maintenances and revisions of timepieces.

To this end, the object of the invention is a portable modular unit for inspecting in a timepiece the presence of a lubricating agent, or of an epilame, having fluorescent markers, from an excitation luminous flux of white light, said portable modular unit being characterised in that it comprises an optical housing forming a first module, a portable white light source emitting an excitation luminous flux forming a second module, a portable magnifying device forming a third module; said optical housing supporting:

an excitation filter configured to select in the excitation luminous flux of said portable white light source, the wavelength range suitable for the excitation of the fluorescent markers of the lubricating agent or of the epilame to be inspected, and to transmit a filtered excitation luminous flux;

a dichroic filter configured to reflect said filtered excitation luminous flux and to orient said filtered excitation luminous flux in the direction of an inspection opening capable of being positioned opposite said timepiece, said dichroic filter also being configured to allow a reflection luminous flux emitted by said timepiece under excitation of said filtered excitation luminous flux to pass through;

an emission filter configured to filter the reflection luminous flux and transmit a fluorescence luminous flux corresponding to the fluorescence of the fluorescent markers of said lubricating agent or of the epilame to be inspected;

said optical housing comprising:

a first mounting interface for removably mounting said portable white light source on the optical housing, the first mounting interface being configured so that said excitation luminous flux emitted by said portable white light source is directed in the direction of said excitation filter;

a second mounting interface for removably mounting said portable magnifying device on the optical housing, said second mounting interface being configured so that said magnifying device is opposite the inspection opening.

Further to the features mentioned in the preceding paragraph, the portable modular unit of the invention may have one or more additional features from the following, considered individually or according to any technically possible combinations:

the first mounting interface and/or the second mounting interface are configured to perform a mechanical and/or magnetic effect coupling; thus, the mounting is simple to perform;

said first mounting interface is configured so that the excitation luminous flux emitted by said portable white light source is oriented perpendicularly to the excitation filter;

said portable white light source is a torch or a penlight; thus, it is not necessary to obtain a specific and expensive light source, a simple torch or a penlight makes it possible to excite the fluorescent markers of a fluorescent lubricating agent;

said portable magnifying device is a watchmakers' eyeglass;

said dichroic filter has an inclination of 45° in relation to the filtered excitation luminous flux;

said optical housing is made of polymer material or of composite material; thus, the manufacturing costs are minimised;

said optical housing is made of polymer material by 3D printing; thus, the manufacturing of such an optical housing and portable modular unit is facilitated, economical and accessible to as many people as possible; indeed, it is sufficient to subsequently integrate optical filters available on the market;

the first mounting interface and/or the second mounting interface include locking means for reversibly locking the coupling of said portable white light source and/or of said magnifying device on said optical housing; thus, the mounting of various modules is secured, which makes it possible to overcome an undesired uncoupling during the use of such a portable modular unit;

the second mounting interface comprises notches to facilitate the positioning and/or the dismantling of the emission filter.

BRIEF DESCRIPTION OF THE FIGURES

The aims, advantages and features of the present invention will become apparent upon reading the following detailed description making reference to the following figures.

In all of the figures, the common elements bear the same reference number unless otherwise specified.

DETAILED DESCRIPTION OF THE INVENTION

Figure 1:
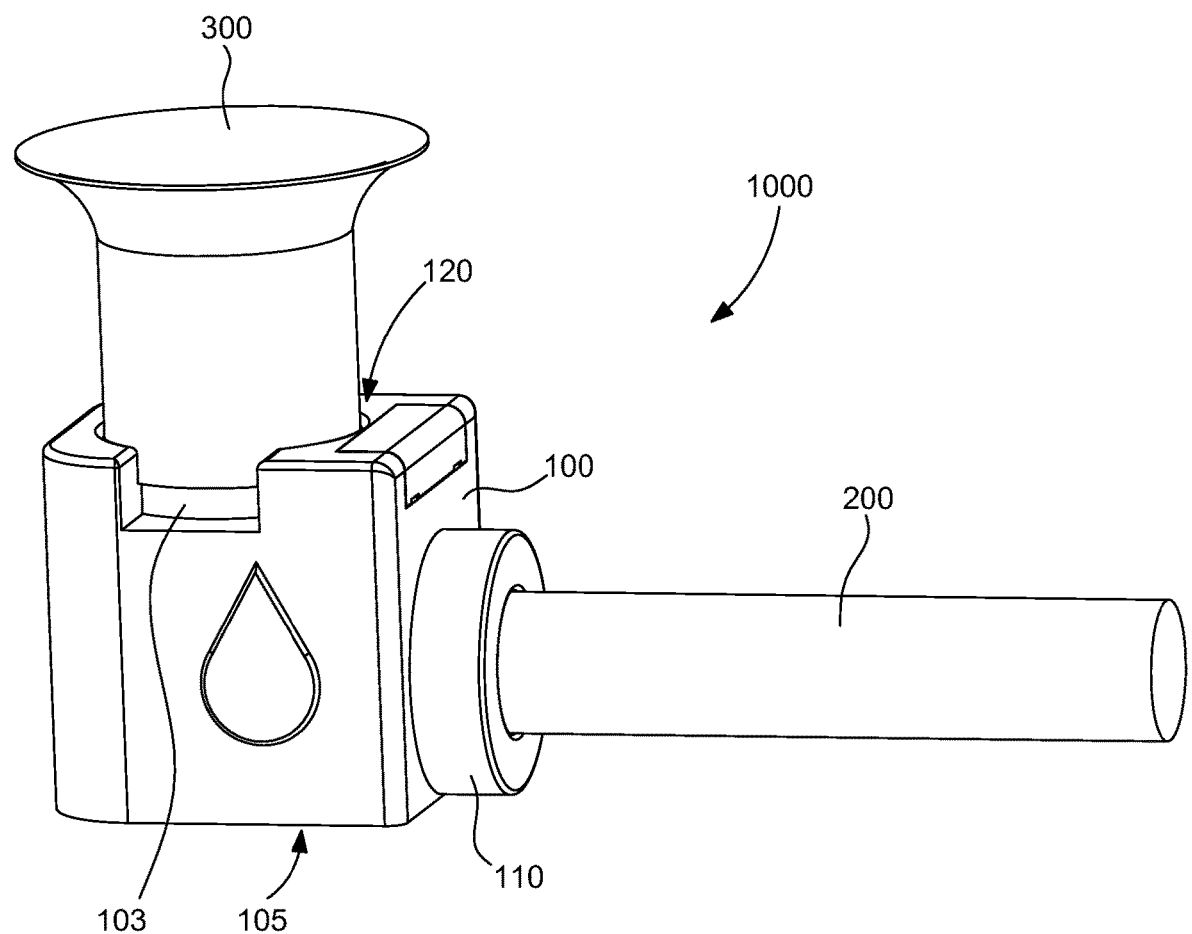
FIG. 1 schematically shows a perspective view of an example of embodiment of a portable modular unit according to the invention.

FIG. 1 shows an example of embodiment of a portable modular unit 1000 according to the invention, the various modules of the unit being assembled with one another in this figure.

Figure 2:
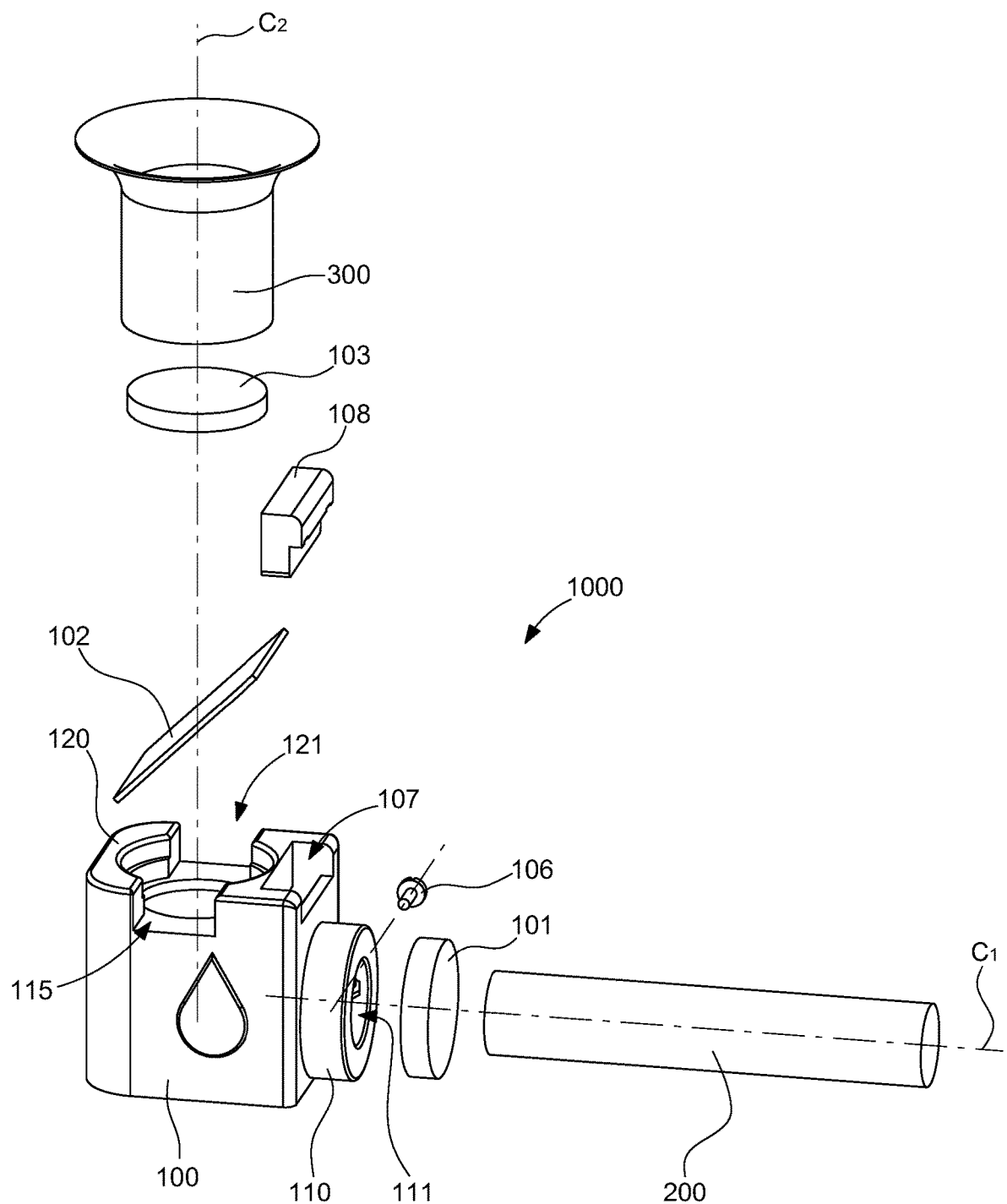
FIG. 2 schematically represents an exploded view of the portable modular unit illustrated in FIG. 1.

FIG. 2 shows an exploded view of the portable modular unit 1000 according to the invention.

Figure 3:
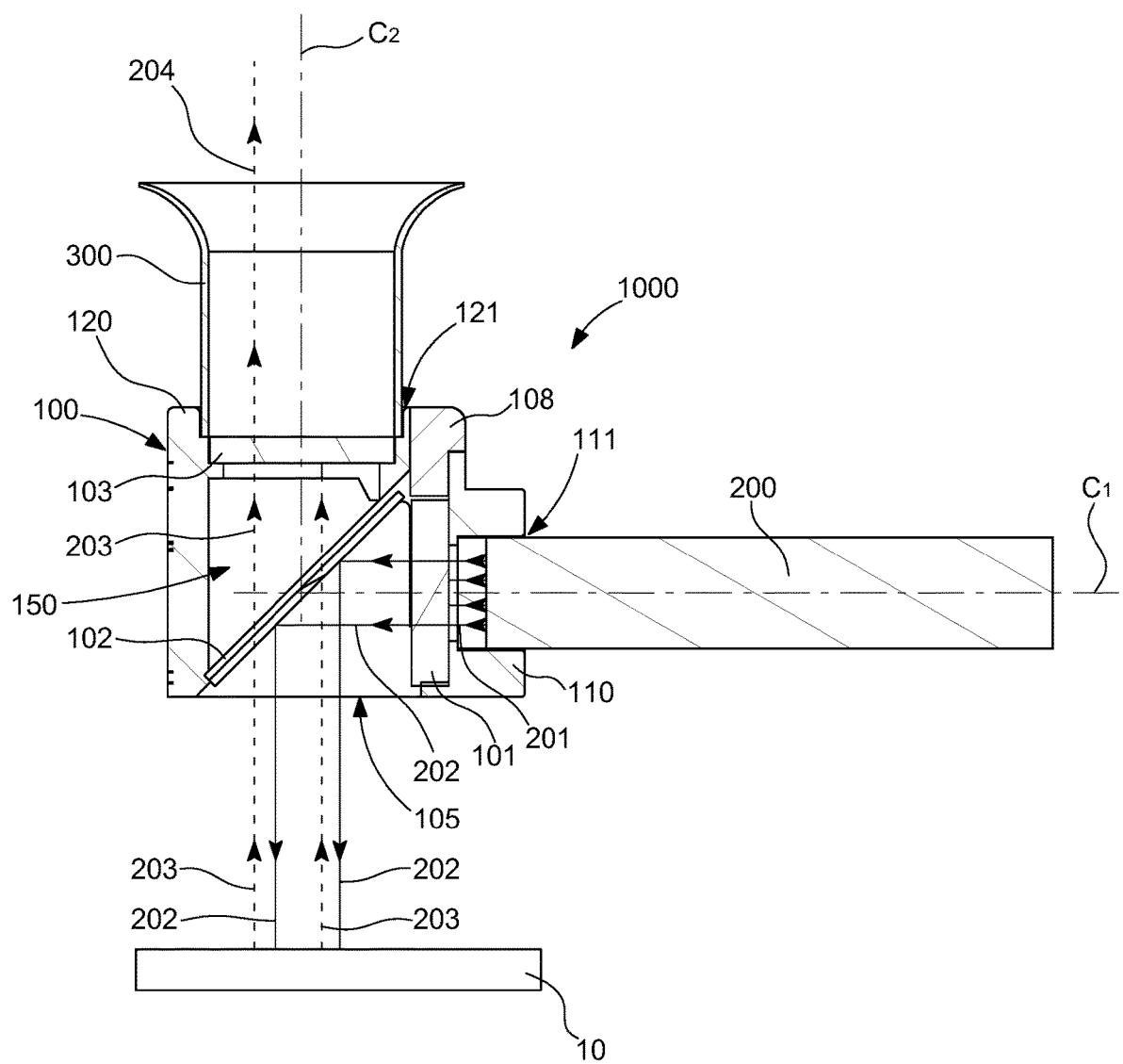
FIG. 3 schematically represents a sagittal sectional view of the portable modular unit illustrated in FIG. 1.

FIG. 3 is a sagittal sectional view of the portable modular unit 1000 shown in FIG. 1.

With reference to FIGS. 1 to 3, the portable modular unit 1000 according to the invention makes it possible to inspect a timepiece 10 (shown in FIG. 3), such as for example a horological movement.

The portable modular unit 1000 according to the invention more particularly makes it possible to inspect the presence or not, in sufficient quantity or not, of a lubricating agent or of an epilame having fluorescent markers reacting to a luminous excitation, by means of a white light source.

In the present application, lubricating agent means a grease, an oil or any other lubricating substance conventionally used in the field of horology.

The portable modular unit 1000 is an assembly of three distinct modules.

A first module of the portable modular unit 1000 is formed by an optical housing 100 comprising the various optical elements necessary for the excitation of fluorescent markers and for the transmission of a fluorescence luminous flux resulting from this excitation.

A second module of the portable modular unit 1000 is formed by a portable white light source 200, commonly used, such as for example a torch or a penlight. The portable white light source 200 obviously emits a luminous flux of white light at the request of the user. This flux is subsequently called and referenced as excitation luminous flux 201.

A third module of the portable modular unit 1000 is formed by a portable magnifying device 300 commonly used in the field of horology, such as for example a watchmakers' eyeglass.

The combination of these three modules, and their interfacing removably and reversibly makes it possible to easily and economically construct a portable modular unit 1000 for the inspection of a lubricating agent or of an epilame having fluorescent markers by means of a white light source. The portable modular unit 1000 according to the invention makes it possible to meet the various drawbacks related to the use of luminous sources harmful for eyes through the use of a portable white light source 200 commonly used easily available in a horological workshop for example.

The optical housing 100 comprises a first mounting interface 110 making it possible to couple, removably and reversibly, the portable white light source 200.

The first mounting interface 110 is an interface of the female type comprising a first cavity 111, for example of cylindrical shape, and more particularly of circular cylindrical shape in such a way as to correspond to the circular shape of the portable white light source 200 formed by a torch or a penlight. The torch constitutes the male portion of the assembly. The portable white light source 200 is thus mounted on the housing 100 by inserting an end portion of the portable white light source 200 into the first cavity 111.

The first cavity 111 of the first mounting interface 110 communicates with an inner chamber 150 arranged inside the optical housing 100.

The optical housing 100 comprises a second mounting interface 120 making it possible to couple, removably and reversibly, the magnifying device 300, of the watchmakers' eyeglass type.

The second mounting interface 120 is also an interface of the female type comprising a second cavity 121, for example of cylindrical shape, and more particularly of circular cylindrical shape, in such a way as to correspond to the circular shape of the magnifying device 300 of the watchmakers' eyeglass type. The magnifying device 300 constitutes the male portion of the assembly. The magnifying device 300 is thus mounted on the housing 100 by inserting an end portion of the magnifying device 300 into the second cavity 121.

The second cavity 121 of the second mounting interface 120 also communicates with the inner chamber 150 of the optical housing 100.

The inner chamber 150 is divided into two portions by a dichroic filter 102 positioned inside the inner chamber 150.

The first cavity 111 extends along a first axis of revolution C1 and the second cavity 121 extends along a second axis of revolution C2, the first cavity 111 and the second cavity 121 being arranged so that their respective axis of revolution C1, C2 are orthogonal and cross at the inner chamber 150.

The dichroic filter 102 is positioned substantially at the intersection of these two axes of revolution C1, C2, according to a 45° angle in relation to each of these axes of revolution C1, C2.

The optical housing 100 comprises a first slot for receiving and supporting an excitation filter 101 having properties to select in the excitation luminous flux 201, coming from the white light source 200, a wavelength range suitable for the excitation of the fluorescent markers of the lubricating agent or of the epilame to be inspected in the timepiece 10, and to transmit a filtered excitation luminous flux 202 in the inner chamber 150.

The excitation filter 101 is advantageously positioned perpendicularly to the axis of revolution C1 of the cavity 111 between the inner chamber 150 and the first mounting interface 110 so that the filtered excitation luminous flux 202 can propagate inside the inner chamber 150 of the optical housing 100 and arrive with an angle close to 45° on the dichroic filter 102.

The excitation filter 101 thus forms the interface between the inner chamber 150 and the first cavity 111 of the first mounting interface 110 communicating with the outside of the optical housing 100.

The dichroic filter 102 comprises properties to reflect the filtered excitation luminous flux 202 arriving in the inner chamber 150 and to orient it, in view of its inclination, in the direction of an inspection opening 105 located opposite the second mounting interface 120 receiving the magnifying device 300.

The dichroic filter 102 also has properties to allow a resulting reflection luminous flux 203, emitted by reflection by the timepiece 10 under the excitation of the filtered excitation luminous flux 202, to pass through.

The optical housing 100 comprises a second slot for receiving and supporting an emission filter 103 comprising properties to filter the reflection luminous flux 203 and to only transmit a fluorescence luminous flux 204 corresponding to the fluorescence of the fluorescent markers of the lubricating agent or of the epilame to be inspected.

The emission filter 103 is advantageously positioned perpendicularly to the axis of revolution C2 of the cavity 121 between the inner chamber 150 and the second mounting interface 120 in such a way as to filter the reflection luminous flux 203 and to transmit a fluorescence luminous flux 204 inside the second cavity 121 of the second mounting interface 120 of the housing 100 and through the magnifying device 300.

Thus, the emission filter 103 forms the interface between the inner chamber 150 and the second cavity 121 of the second mounting interface 120 communicating with the outside of the optical housing 100.

The first mounting interface 110 and the second mounting interface 120 are configured to perform a mechanical coupling.

The mechanical coupling is for example ensured by the particular shape and/or the material of the first mounting interface 110 and of the second mounting interface 120.

By way of example, the first mounting interface 110 and/or the second mounting interface 120 may have at least one portion made of flexible polymer material having elastic properties, or made of an elastomer material making it possible to exert a retention force by elastic or viscoelastic response of the material around the portable white light source 200 and/or the magnifying device 300.

The first cavity 111 of the first mounting interface 110 and/or the second cavity 121 of the second mounting interface 120 may also have at the peripheral wall delimiting the cavity 111, 121, a coating or an elastomer seal that may improve the friction and/or the holding in position of the portable white light source 200 or of the magnifying device 300.

According to one alternative embodiment or in addition to a mechanical coupling, such as described above, the first mounting interface 110 and/or the second mounting interface 120 are configured to perform a magnetic effect coupling. In this case, the first interface 110 and/or the second interface 120 comprise a portion made of magnetic material or a permanent magnet lodged or embedded at the first mounting interface 110 and/or the second mounting interface 120. This alternative embodiment is particularly interesting when the portable white light source 200 or the magnifying device 300 has at least one portion made of ferromagnetic material. Thus, the coupling is ensured and facilitated by the magnetic attraction.

The first mounting interface 110 and the second mounting interface 120 may further comprise locking means to provisionally and reversibly ensure the locking of the various modules, respectively of the portable white light source 200 and of the magnifying device 300 in position on the optical housing 100, and thus secure the mounting of the modules.

The locking means are for example screwing locking means, bayonet locking means.

The locking means are for example formed by a locking member 106 having a mounting head and a threaded body cooperating with a threaded opening arranged according to a radial direction at a mounting interface.

In the example of embodiment illustrated in FIGS. 1 to 3, the locking member 106 cooperates with a threaded opening arranged on the perimeter of the first mounting interface 110 in such a way as to lock, by screwing of the locking member 106, the portable white light source 200 in position on the optical housing 100.

Of course, such a locking member in cooperation with a threaded opening may be arranged at the second mounting interface 120 for the locking of the magnifying device 300 in position on the optical housing 100

The first mounting interface 110 and the second mounting interface 120 may be identical or different, and ensure an identical or different coupling. Furthermore, the first mounting interface 110 and the second mounting interface 120 may comprise identical or different locking means.

Although the presence of additional locking means makes it possible to secure the coupling and the holding in position of the various modules 200, 300, particularly during various manipulations of the portable modular unit 1000, these locking means are not mandatory for ensuring the coupling and the holding in position of the portable white light source 200 or of the magnifying device 300 on the optical housing 1000. Indeed, it is sufficient that the first mounting interface 110 and/or the second mounting interface 120 has(have) a cavity 111, 121 the dimensions of which are configured to ensure the insertion and the holding in position of the portable white light source 200 and of the magnifying device 300, with the appropriate mounting plays. Thus, with a sufficiently important length of the cavity 111, 121 and an appropriate diameter, the portable white light source 200 and the magnifying device 300 may perfectly be removably mounted on the optical housing 100 and held in position during the use of the portable modular unit 1000.

In the example of embodiment illustrated, the optical housing 100 further comprises a hole 107 for the positioning of the excitation filter 101 in its slot inside the optical housing 100. The slot-shaped hole 107 makes it possible to facilitate the positioning of the excitation filter 101 in its slot between the inner chamber 150 and the cavity 111 of the first mounting interface 110.

The optical housing 100 may comprise a bush 108 coming to block the hole 107 after the positioning of the excitation filter 101. The bush 108 may be configured to exert a slight compression on the excitation filter 101 in such a way as to ensure the holding in position of the excitation filter in its slot.

The optical housing 100 may also comprise notches 115 arranged at the mounting interfaces 110, 120 to facilitate the mounting and/or the extraction of the optical filters. In the example of embodiment illustrated in FIGS. 1 to 3, such notches 115 are shown only at the second mounting interface 120 receiving the magnifying device 300. At the second mounting interface 120, the notches 115 make it possible to facilitate the manipulation in view of the mounting or of the extraction of the emission filter 103 positioned at the bottom of the second cavity 121. These notches 115 are particularly useful when the emission filter 103 to be mounted or to be extracted has dimensions less than the dimensions of the second cavity 121 receiving the magnifying device 300.

The optical housing 100 is advantageously made of polymer material or of composite material. By way of example, the optical housing 100 is made of polymer material, for example via a three-dimensional printing method in such a way as to facilitate the manufacturing and the accessibility of such an optical housing 100. Once the housing has been produced in 3D printing, it is easy to integrate the various optical filters 101, 102, 103, available on the market, in various slots provided for this purpose at the optical housing 100.

The invention claimed is:

1. A portable modular unit (1000) for inspecting in a timepiece (10) the presence of a lubricating agent, or of an epilame, having fluorescent markers, from an excitation luminous flux of white light, wherein said portable modular unit (1000) comprises an optical housing (100) forming a first module, a portable white light source (200) emitting an excitation luminous flux (201) forming a second module, and a portable magnifying device (300) forming a third module;

said optical housing (100) supporting:
an excitation filter (101) configured to select in the excitation luminous flux (201) of said portable white light source (200) a wavelength that corresponds to an excitation wavelength of the fluorescent markers of the lubricating agent or of the epilame to be inspected, and to transmit a filtered excitation luminous flux (202);
a dichroic filter (102) configured to reflect said filtered excitation luminous flux (202) and to orient said filtered excitation luminous flux (202) in the direction of an inspection opening (105) capable of being positioned opposite said timepiece (10), said dichroic filter (102) also being configured to allow a reflection luminous flux (203) emitted by said timepiece (10) under excitation of said filtered excitation luminous flux (202) to pass through;
an emission filter (103) configured to filter the reflection luminous flux (203) and transmit a fluorescence luminous flux (204) corresponding to the fluorescence of the fluorescent markers of said lubricating agent or of the epilame to be inspected;

said optical housing (100) comprising:
a first mounting interface (110) comprising a first cavity for removably mounting said portable white light source (200) on the optical housing (100) such that the portable white light source (200) is attachable to and detachable from the optical housing (100), the first mounting interface (110) being configured so that said excitation luminous flux (201) emitted by said portable white light source (200) is directed in the direction of said excitation filter (101);
a second mounting interface (120) comprising a second cavity for removably mounting said portable magnifying device (300) on the optical housing (100) such that the portable magnifying device (300) is attachable to and detachable from the optical housing (100), said second mounting interface (120) being configured so that said magnifying device (300) is opposite the inspection opening (105),
wherein the optical housing (100) further comprises a first slot for receiving and supporting an excitation filter (101).

2. The portable modular unit (1000) for inspecting in a timepiece (10) the presence of a lubricating agent or of an epilame having fluorescent markers from an excitation luminous flux of white light according to claim 1, wherein the first mounting interface (110) and/or the second mounting interface (120) are configured to perform a mechanical and/or magnetic effect coupling.

3. The portable modular unit (1000) for inspecting in a timepiece (10) the presence of a lubricating agent or of an epilame having fluorescent markers from an excitation luminous flux of white light according to claim 1, wherein said first mounting interface (110) is configured so that the excitation luminous flux (201) emitted by said portable white light source (200) is oriented perpendicularly to the excitation filter (101).

4. The portable modular unit (1000) for inspecting in a timepiece (10) the presence of a lubricating agent or of an epilame having fluorescent markers from an excitation luminous flux of white light according to claim 1, wherein said portable white light source (200) is a penlight.

5. The portable modular unit (1000) for inspecting in a timepiece (10) the presence of a lubricating agent or of an epilame having fluorescent markers from an excitation luminous flux of white light according to claim 1, wherein said portable magnifying device (300) is a watchmakers' eyeglass.

6. The portable modular unit (1000) for inspecting in a timepiece (10) the presence of a lubricating agent or of an epilame having fluorescent markers from an excitation luminous flux of white light according to claim 1, wherein said dichroic filter (102) has an inclination of 45° in relation to the filtered excitation luminous flux (202).

7. The portable modular unit (1000) for inspecting in a timepiece (10) the presence of a lubricating agent or of an epilame having fluorescent markers from an excitation luminous flux of white light according to claim 1, wherein said optical housing (100) is made of polymer material or of composite material.

8. The portable modular unit (1000) for inspecting in a timepiece (10) the presence of a lubricating agent or of an epilame having fluorescent markers from an excitation luminous flux of white light according to claim 1, wherein said optical housing (100) is made of polymer material by 3D printing.

9. The portable modular unit (1000) for inspecting in a timepiece (10) the presence of a lubricating agent or of an epilame having fluorescent markers from an excitation luminous flux of white light according to claim 1, wherein the first mounting interface (110) and/or the second mounting interface (120) comprise locking means to reversibly lock the coupling of said portable white light source (200) and/or of said magnifying device (300) on said optical housing (100).

10. The portable modular unit (1000) for inspecting in a timepiece (10) the presence of a lubricating agent or of an epilame having fluorescent markers from an excitation luminous flux of white light according to claim 1, wherein the second mounting interface (120) comprises notches (115) to facilitate the positioning and/or the dismantling of the emission filter (101).

11. The portable modular unit (1000) for inspecting in a timepiece (10) the presence of a lubricating agent or of an epilame having fluorescent markers from an excitation luminous flux of white light according to claim 1, wherein the optical housing (100) further comprises a hole (107) for positioning of the excitation filter (101) in the first slot inside of the optical housing (100).

12. A portable modular unit (1000) for inspecting in a timepiece (10) the presence of a lubricating agent, or of an epilame, having fluorescent markers, from an excitation luminous flux of white light, wherein said portable modular unit (1000) comprises an optical housing (100) forming a first module, a portable white light source (200) emitting an excitation luminous flux (201) forming a second module, and a portable magnifying device (300) forming a third module;

said optical housing (100) supporting:

an excitation filter (101) configured to select in the excitation luminous flux (201) of said portable white light source (200) a wavelength that corresponds to an excitation wavelength of the fluorescent markers of the lubricating agent or of the epilame to be inspected, and to transmit a filtered excitation luminous flux (202);

a dichroic filter (102) configured to reflect said filtered excitation luminous flux (202) and to orient said filtered excitation luminous flux (202) in the direction of an inspection opening (105) capable of being positioned opposite said timepiece (10), said dichroic filter (102) also being configured to allow a reflection luminous flux (203) emitted by said timepiece (10) under excitation of said filtered excitation luminous flux (202) to pass through;

an emission filter (103) configured to filter the reflection luminous flux (203) and transmit a fluorescence luminous flux (204) corresponding to the fluorescence of the fluorescent markers of said lubricating agent or of the epilame to be inspected;

said optical housing (100) comprising:

a first mounting interface (110) for removably mounting said portable white light source (200) on the optical housing (100), the first mounting interface (110) being configured so that said excitation luminous flux (201) emitted by said portable white light source (200) is directed in the direction of said excitation filter (101);

a second mounting interface (120) for removably mounting said portable magnifying device (300) on the optical housing (100), said second mounting interface (120) being configured so that said magnifying device (300) is opposite the inspection opening (105), wherein said portable white light source (200) is a torch.

\* \* \* \* \*